(12) United States Patent
Yamada et al.

(10) Patent No.: US 11,179,082 B2
(45) Date of Patent: Nov. 23, 2021

(54) DRIVING ASSISTANCE DEVICE

(71) Applicant: MAZDA MOTOR CORPORATION, Hiroshima (JP)

(72) Inventors: Naoki Yamada, Hiroshima (JP); Kazuhiro Takemura, Hiroshima (JP); Tadayuki Niibe, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 279 days.

(21) Appl. No.: 16/342,931

(22) PCT Filed: Sep. 25, 2017

(86) PCT No.: PCT/JP2017/034544
§ 371 (c)(1),
(2) Date: Apr. 17, 2019

(87) PCT Pub. No.: WO2018/074148
PCT Pub. Date: Apr. 26, 2018

(65) Prior Publication Data
US 2020/0054263 A1 Feb. 20, 2020

(30) Foreign Application Priority Data
Oct. 19, 2016 (JP) .............................. JP2016-204890

(51) Int. Cl.
*G06F 7/00* (2006.01)
*A61B 5/18* (2006.01)
(Continued)

(52) U.S. Cl.
CPC ................ *A61B 5/18* (2013.01); *A61B 5/024* (2013.01); *A61B 5/6893* (2013.01); *A61M 21/00* (2013.01);
(Continued)

(58) Field of Classification Search
CPC ......... A61B 5/18; A61B 5/024; A61B 5/6893; A61M 21/00; A61M 2021/0027;
(Continued)

(56) References Cited

U.S. PATENT DOCUMENTS 8,275,497 B2 * 9/2012 Koch-Groeber ...... B60W 40/04
701/10
9,475,502 B2 * 10/2016 Fung .................... A61B 5/6893
(Continued)

FOREIGN PATENT DOCUMENTS

| JP | 2007-022117 A | 2/2007 |
| JP | 2007-038911 A | 2/2007 |

(Continued)

OTHER PUBLICATIONS

Communication pursuant to Article 94(3) EPC issued by the European Patent Office dated May 27, 2020, which corresponds to European Patent Application No. 17 861 565.4-1132 and is related to U.S. Appl. No. 16/342,931.
(Continued)

*Primary Examiner* — Zhen Y Wu
(74) *Attorney, Agent, or Firm* — Studebaker & Brackett PC

(57) ABSTRACT

A driving assistance device (1) includes: a somatic nervous system activity detector (11) detecting a somatic nervous system activity, which is a physical activity, of a driver in association with steering of a vehicle; an autonomic nervous system activity detector (12) detecting an autonomic nervous system activity, which is a mental activity, of the driver in association with the steering of the vehicle; a somatic nervous system activity controller (perception amount controller (2)) which is operable to control the somatic nervous system activity; an autonomic nervous system activity controller (sound effect generator (3)) which is operable to
(Continued)

control the autonomic nervous system activity; and a psychosomatic state controller (balance controller (14)). The psychosomatic state controller causes the somatic nervous system activity controller and the autonomic nervous system activity controller to operate such that the two activities shift to the same side with respect to increase and decrease.

5 Claims, 9 Drawing Sheets

(51) Int. Cl.
*A61B 5/024* (2006.01)
*A61B 5/00* (2006.01)
*A61M 21/00* (2006.01)
*B60W 40/08* (2012.01)
*B60W 50/08* (2020.01)

(52) U.S. Cl.
CPC ............ *B60W 40/08* (2013.01); *B60W 50/08* (2013.01); *A61M 2021/0027* (2013.01); *A61M 2021/0083* (2013.01); *A61M 2205/3303* (2013.01); *B60W 2040/0872* (2013.01)

(58) Field of Classification Search
CPC . A61M 2021/0083; A61M 2205/3303; B60W 40/08; B60W 50/08; B60W 2040/0872
USPC .............................................. 340/36; 701/36
See application file for complete search history.

(56) References Cited

U.S. PATENT DOCUMENTS

| | | | |
|---|---|---|---|
| 10,399,565 B2 * | 9/2019 | Posch | B60W 50/10 |
| 10,399,575 B2 * | 9/2019 | Spasojevic | A61B 5/6893 |
| 2007/0182529 A1 * | 8/2007 | Dobler | B60K 28/066 |
| | | | 340/438 |
| 2014/0039757 A1 * | 2/2014 | Prakah-Asante | G06F 7/00 |
| | | | 701/36 |
| 2014/0104405 A1 * | 4/2014 | Weidl | G06K 9/00845 |
| | | | 348/77 |
| 2014/0221781 A1 * | 8/2014 | Schrauf | A61B 5/02055 |
| | | | 600/301 |
| 2015/0266484 A1 * | 9/2015 | Moran | B60W 40/09 |
| | | | 340/576 |
| 2015/0307105 A1 * | 10/2015 | Huber | B60W 50/14 |
| | | | 340/576 |
| 2017/0368936 A1 * | 12/2017 | Kojima | B60W 40/09 |
| 2018/0050696 A1 * | 2/2018 | Misu | A61B 5/0077 |

FOREIGN PATENT DOCUMENTS

| | | |
|---|---|---|
| JP | 2007-512989 A | 5/2007 |
| JP | 2008-125801 A | 6/2008 |
| JP | 2010-142593 A | 7/2010 |
| JP | 2011-143915 A | 7/2011 |
| JP | 2014-518647 A | 8/2014 |
| WO | 2004/101306 A1 | 11/2004 |

OTHER PUBLICATIONS

International Search Report issued in PCT/JP2017/034544; dated Nov. 28, 2017.

* cited by examiner

DRIVING ASSISTANCE DEVICE

TECHNICAL FIELD

The present invention relates to driving assistance devices that assist driving of drivers of vehicles and, in particular, to a driving assistance device that determines a psychosomatic state of a driver of a vehicle based on a somatic nervous system activity and an autonomic nervous system activity of the driver and activates the psychosomatic state.

BACKGROUND ART

Conventionally, there has been known a driving assistance device that provides assistance for driving of a vehicle driver from the vehicle by detecting a psychosomatic activity state of the driver of the vehicle via bionomic activity information.

Patent Document 1 discloses a warning system for a vehicle. The warning system sets a determination condition value A representing a driving condition of the driver by detecting that the eyelids of the driver have been inactive for a fixed period of time or longer, sets a determination condition value B representing a driving pattern of the driver by detecting that a fixed driving pattern has been continuing for a fixed period of time or longer, sets a determination condition value C representing a physical condition of the driver by detecting that each value of a body temperature, a perspiration amount, and a pulse is a fixed value or more, sets a determination condition value D representing a driving condition of the driver by detecting a frequency of looking-aside of the driver. The determination condition values A to D are added up, and if the resultant value is equal to or greater than a threshold value X 0, a reaction time of the driver is detected, and if the reaction time is equal to or greater than a threshold value TO, timing at which warning is issued is advanced.

Incidentally, it has been known that the peripheral nervous system of a human is anatomically classified into the cerebral nervous system that consists of 12 nerves pairs emerging from a brain and the spinal nervous system that consists of 31 nerves pairs emerging from a spinal cord, and is functionally classified into the somatic nervous system that is related to animal functionality and the autonomic nervous system that is related to vegetable functionality.

Somatic nerves are nerves to perform voluntary movement controlled by a cerebral neocortex (consciousness) and control efferent motor nerves that control legs, arms, and the like and afferent motor nerves that transmit sensory information from sensory organs such as ears and eyes to the brain. Autonomic nerves are nerves to perform intracorporeal adjustment controlled by an old brain (unconsciousness), are mainly related to a mental state, and control the sympathetic nerves that activate the actions of the brain, the heart, and the like while suppressing the actions of the viscera and the like and the parasympathetic nerves that suppress the actions of the brain, the hear, and the like while activating the actions of the viscera and the like.

CITATION LIST

Patent Document

Patent Document 1: Japanese Unexamined Patent Publication No. 2007-038911

SUMMARY OF THE INVENTION

Technical Problem

Based on the resultant value (an overall determination value) obtained by adding the determination condition value A related to motion of the eyelids of the driver, the determination condition value B related to the driving pattern, the determination condition value C related to the pulse and the like, and the determination condition value D related to the frequency of looking-aside, the warning system for a vehicle of Patent Document 1 comprehensively determines a degree of fatigue, a degree of wakefulness, and a degree of concentration, and estimates a likelihood of delay in operation reaction in avoiding an emergency state.

However, according to Patent Document 1, since the determination condition values A and C that are pieces of information pertinent to the autonomic nervous system and the determination condition values B and D that are pieces of information pertinent to the somatic nervous system are added up as parameters on the same level in a single uniform manner, it is difficult to determine the psychosomatic state of the driver with a high accuracy.

Specifically, for a driver having high driving skill, even when a mental state (the determination condition values A and C) of the driver is slightly low, it is likely that an overall determination value becomes high while the low mental state is not taken into consideration since the driving skill (the determination condition values B and D) is high. Conversely, for a driver having low driving skill, even when a mental state (the determination condition values A and C) of the driver is slightly high, it is likely that an overall determination value becomes low while the high mental state is not taken into consideration since the driving skill (the determination condition values B and D) is low.

It is presumed that a driver drives a vehicle, having a specific steering image based on the past experience (a sense of expectation) and when the driver has achieved the steering performance just as imaged (a sense of achievement), intrinsic motivation is generated with which the driver will challenge the next driving with self-confidence (a sense of self-efficacy).

FIG. 11 shows an activation circle comprised of three factors, namely, the sense of expectation, the sense of achievement, and the sense of self-efficacy. A state in which the three factors smoothly circulate (clockwise) in the activation circle represents a state in which both mind (a psyche) and a body are activated through driving operation, resulting in contribution to enhancement in safety.

However, for smoothly circulating the sense of expectation, the sense of achievement, and the sense of self-efficacy in the activation circle, it is not easy to visualize a psychosomatic state of the driver with numerical values. In addition, in order to smoothly circulate the factors in the activation circle, it is required to establish a potent method which allows the intrinsic motivation to be generated and the sense of self-efficacy to be enhanced.

The present inventors have repeated eager researches. As a result, the present inventors have found that the sense of expectation can be visually observed by using a mental activity (an autonomic nervous system activity, i.e. a degree of activation of autonomic nervous system) which is a physical internal index as a parameter, and the sense of achievement can be visually observed by using a physical activity (a somatic nervous system activity, i.e., a degree of activation of somatic nervous system) which is each of perceptive, motional, and action indices as a parameter.

In view of the foregoing background, it is therefore an object of the present invention to provide a driving assistance device which is operable to activate a psychosomatic state of a driver via steering of a vehicle by visualizing a sense of expectation and a sense of achievement of the driver.

Solution to the Problem

In order to achieve the above object, the present invention is directed to a driving assistance device for assisting driving of a driver of a vehicle. The driving assistance device includes: a somatic nervous system activity detector detecting a somatic nervous system activity, which is a physical activity, of the driver in association with steering of the vehicle; an autonomic nervous system activity detector detecting an autonomic nervous system activity, which is a mental activity, of the driver in association with the steering of the vehicle; a somatic nervous system activity controller being operable to control the somatic nervous system activity; an autonomic nervous system activity controller being operable to control the autonomic nervous system activity; and a psychosomatic state controller controlling the somatic nervous system activity controller and the autonomic nervous system activity controller based on the somatic nervous system activity detected by the somatic nervous system activity detector and the autonomic nervous system activity detected by the autonomic nervous system activity detector. The psychosomatic state controller is configured to cause the somatic nervous system activity controller and the autonomic nervous system activity controller to operate such that the somatic nervous system activity and the autonomic nervous system activity shift to a same side with respect to increase and decrease.

The driving assistance device includes: a somatic nervous system activity detector detecting a somatic nervous system activity, which is a physical activity, of a driver in association with steering of a vehicle, of a driver in association with steering of a vehicle; an autonomic nervous system activity detector detecting an autonomic nervous system activity, which is a mental activity, of a driver in association with steering of the vehicle; a somatic nervous system activity controller being operable to control the somatic nervous system activity; an autonomic nervous system activity controller being operable to control the autonomic nervous system activity; and a psychosomatic state controller controlling the somatic nervous system activity controller and the autonomic nervous system activity controller. Therefore, the driving assistance degree of activation is operable to perform the control by visualizing the somatic nervous system activity as numerical values via perception, movement, and action indices, and is operable to perform the control by visualizing the autonomic nervous system activity as numerical values via physical internal indices.

The psychosomatic state controller causes the somatic nervous system activity controller and the autonomic nervous system activity controller to operate such that the somatic nervous system activity and the autonomic nervous system activity shift to the same side with respect to increase and decrease. Therefore, the somatic nervous system activity and the autonomic nervous system activity can be made to have the same tendency of increase or decrease. As a result, the psychosomatic state of the driver can be transitioned to a state in which both his/her mind and body are activated without causing the driver to feel a sense of discomfort.

In one embodiment of the driving assistance device, the psychosomatic state controller is configured to cause the somatic nervous system activity controller and the autonomic nervous system activity controller to operate such that a ratio between the somatic nervous system activity and the autonomic nervous system activity is made constant.

With this configuration, the psychosomatic state of the driver can be easily brought into a state in which the somatic nervous system and the autonomic nervous system are activated in a balanced manner.

In another embodiment of the driving assistance device, a coordinate system is defined by the somatic nervous system activity and the autonomic nervous system activity, a balance zone previously set so as to include part of a balance line on which a ratio between the somatic nervous system activity and the autonomic nervous system activity is constant is provided in the coordinate system. The psychosomatic state controller is configured such that when the somatic nervous system activity and the autonomic nervous system activity are present inside the balance zone, the psychosomatic state controller causes the somatic nervous system activity controller and the autonomic nervous system activity controller to operate such that the somatic nervous system activity and the autonomic nervous system activity shift to the same side with respect to increase and decrease, and when the somatic nervous system activity and the autonomic nervous system activity are present outside the balance zone, the psychosomatic state controller causes the somatic nervous system activity controller and/or the autonomic nervous system activity controller to operate such that the somatic nervous system activity and the autonomic nervous system activity shift to enter the balance zone.

With this configuration, the psychosomatic state of the driver can be observed in the coordinate system where the balance zone A including part of the balance line L representing the state where the somatic nervous system and the autonomic nervous system are balanced, is provided. In addition, the psychosomatic state of the driver can be easily brought into the state in which the somatic nervous system and the autonomic nervous system are activated in the balanced manner.

In the above-described another embodiment, the psychosomatic state controller is configured such that when the somatic nervous system activity and the autonomic nervous system activity are present in a vicinity of an upper end inside the balance zone in the coordinate system for a period of time exceeding a fixed period of time, the psychosomatic state controller causes the somatic nervous system activity controller and the autonomic nervous system activity controller to operate such the somatic nervous system activity and the autonomic nervous system activity increase after having decreased.

This configuration makes it possible to avoid a state in which a load exerted on the driver is high and to achieve both of the psychosomatic activation state and comfortability of the driver.

In further another embodiment of the driving assistance device, the somatic nervous system activity controller is configured to control a reactive force perception amount with respect to an operation amount of the driver, and the autonomic nervous system activity controller is configured to control at least one of an audiovisual perception amount or a response speed with respect to the operation amount of the driver.

This configuration makes it possible to quickly transition the psychosomatic state of the driver to a state in which both the mind and body of the driver are activated.

In yet another embodiment of the driving assistance device, the somatic nervous system activity detector is configured to detect a voluntary movement amount of the driver, and the autonomic nervous system activity detector is configured to detect vital information of the autonomic nervous system of the driver.

This configuration makes it possible to detect the somatic nervous system activity and the autonomic nervous system activity with high accuracy by using numerical values.

Advantages of the Invention

As described above, the driving assistance device of the present invention allows the psychosomatic state of the driver to be activated via the steering of the vehicle by visualizing the sense of expectation and the sense of achievement of the driver via parameters.

DESCRIPTION OF EMBODIMENT

An exemplary embodiment will now be described in detail below, with reference to the accompanying drawings.

Figure 1:
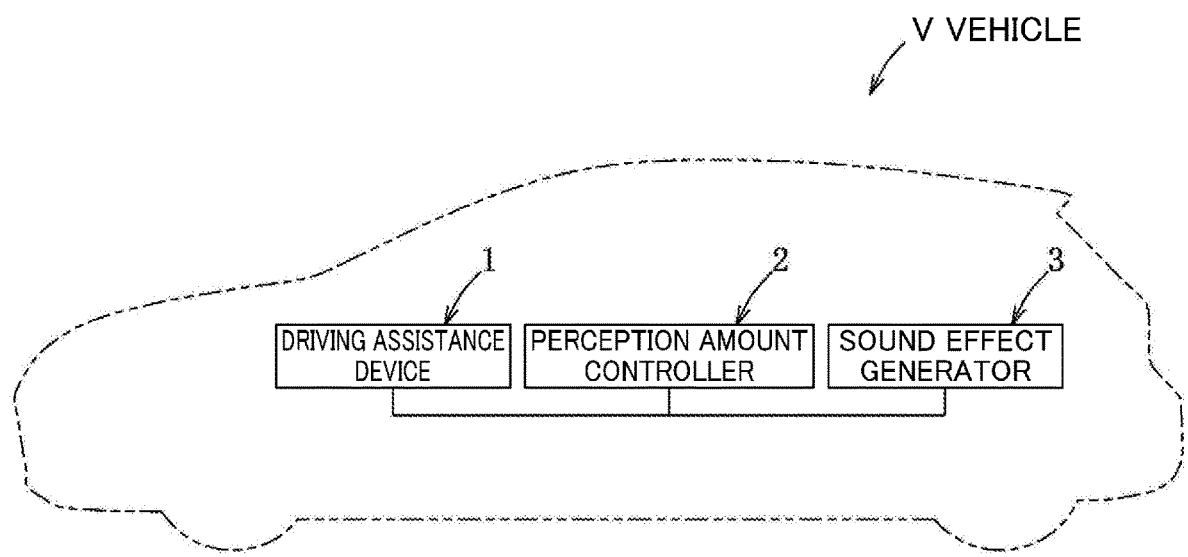
FIG. 1 is a schematic view illustrating a vehicle which includes a driving assistance device according to an exemplary embodiment of the present invention.
Figure 2:
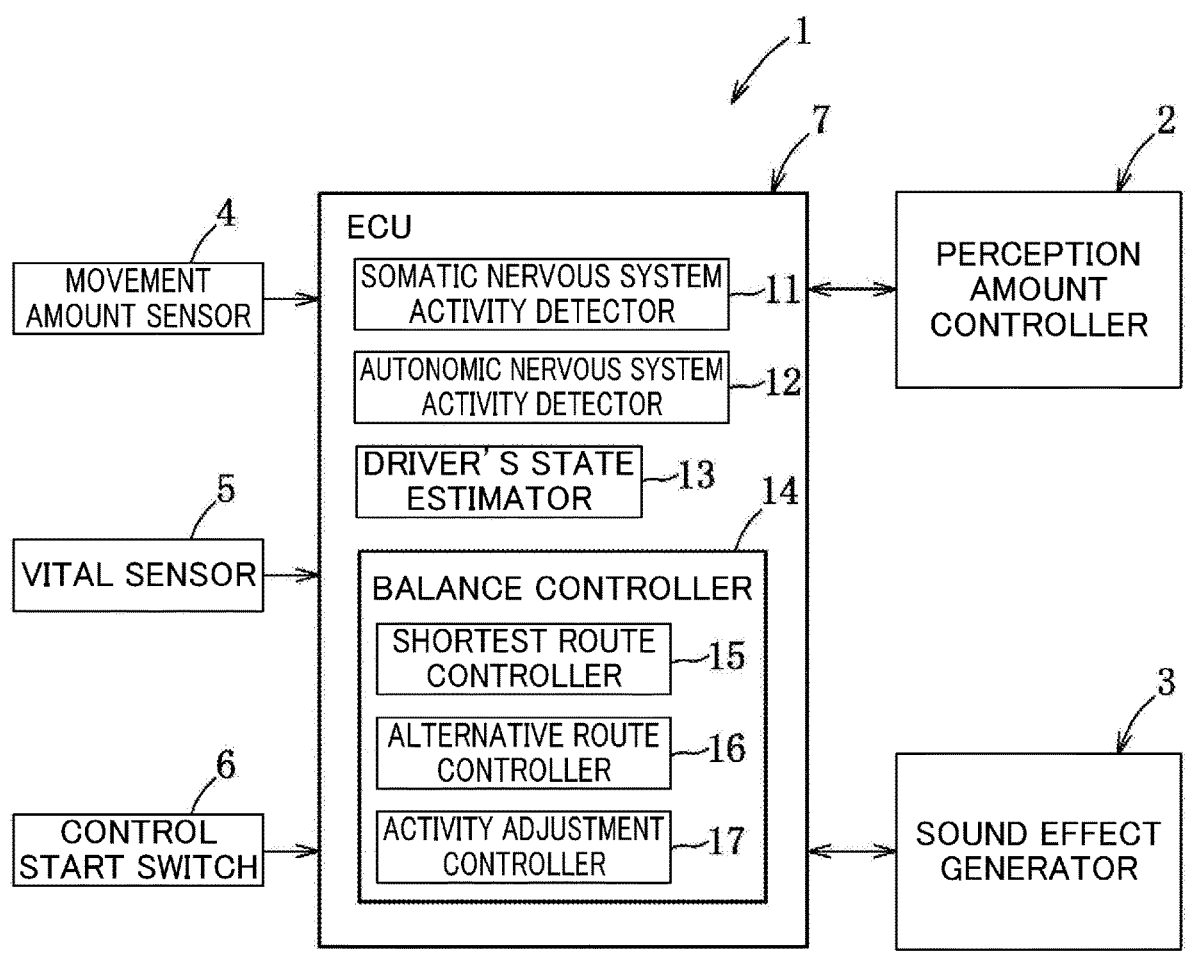
FIG. 2 is a block diagram illustrating the driving assistance device.

As shown in FIGS. 1 and 2, a vehicle V includes: a driving assistance device 1 which is operable to control (and activate) a psychosomatic state of a driver; a perception amount controller 2 which is operable to control operation feelings related to operation apparatuses; and a sound effect generator 3 which is operable to control a following feeling related to behavior of the vehicle V in response to operation of the driver.

The driving assistance device 1 determines a psychosomatic state of the driver based on two indices, namely, a somatic nervous system activity (also referred to as a physical activity) t and an autonomic nervous system activity (also referred to as a mental activity) g, and based on the psychosomatic state determined, causes at least one of the perception amount controller 2 or the sound effect generator 3 to operate, thereby bringing the driver into a state in which both his/her mind and body are active. Therefore, the driving assistance device 1 has a function of determining the psychosomatic state of the driver.

Somatic nerves control efferent motor nerves that control legs, arms, and the like and afferent motor nerves that transmit sensory information from sensory organs such as ears and eyes to a brain.

Therefore, the somatic nervous system activity t can be detected with use of a voluntary movement amount of the driver as a parameter, and is equivalent to a parameter which reflects a sense of achievement of steering performed by the driver.

The voluntary movement amount can be measured based on a muscle activity strength (an operation amount, a reactive force perception amount, and the like), a movement time (an operation time, a driving time, a responding time, a reaction speed, and the like), a sight line movement speed, and the like.

In addition, the somatic nervous system activity t has such properties that the somatic nervous system activity t increases in accordance with an increase in the voluntary movement of the driver, that is, a perception amount of operation (the driver's performance) and decreases in accordance with a decrease in the perception amount of operation.

On the other hand, the autonomic nerves are mainly related to a mental state, and control the sympathetic nerves that activate the actions of a brain, a heart, and the like while suppressing the actions of viscera and the like and the parasympathetic nerves that suppress the actions of the brain, the heart, and the like while activating the actions of the viscera and the like.

Therefore, the autonomic nervous system activity g can be detected with use of vital information of the autonomic nervous system of the driver as a parameter, and is equivalent to a parameter which reflects a sense of expectation of the steering performed by the driver.

The vital information of the autonomic nervous system can be measured based on a heart rate, a blood pressure, perspiration, a pupil diameter, and the like.

In addition, the autonomic nervous system activity g has such properties that the autonomic nervous system activity g increases (activation of the sympathetic nerves and deactivation of the parasympathetic nerves) in accordance with uplift of driving consciousness of the driver, that is, an increase in the following feeling of the behavior of the vehicle V in response to the operation of the driver (the vehicle's performance) and decreases (deactivation of the sympathetic nerves and activation of the parasympathetic nerves) in accordance with a decrease in the following feeling.

As shown in FIG. 2, the driving assistance device 1 includes: the perception amount controller 2; the sound effect generator 3; a movement amount sensor 4 capable of detecting the voluntary movement amount of the driver; a vital sensor 5 capable of detecting the vital information of the autonomic nervous system of the driver directly from the driver; a control start switch 6 capable of switching on and off assistance control by the driving assistance device 1; and an electronic control unit (ECU) 7. Signals from the movement amount sensor 4, the vital sensor 5, and the control start switch 6 are inputted to the ECU 7. The ECU 7 transmits and receives signals to and from an ECU 30 in the perception amount controller 2 and an ECU 53 in the sound effect generator 3. The ECU 30 and the ECU 53 will be described later.

The ECU 7 is a controller including a well-known microcomputer as a base element and includes a central processing unit (CPU) that executes computer programs (including a basic control program such as an OS and application programs which are run on the OS and realize specific functions), a memory configured, for example, as a RAM and a ROM, and an input/output (I/O) bus inputting and outputting electric signals.

The ROM has stored therein a variety of computer programs and data for determining and improving the psychosomatic state of the driver. The RAM is provided with processing regions used when the CPU performs a series of processing.

As shown in FIG. 2, inside the ECU 7, a somatic nervous system activity detector 11, an autonomic nervous system activity detector 12, a driver's state estimator 13, and a balance controller 14 are provided. The somatic nervous system activity detector 11, the autonomic nervous system activity detector 12, the driver's state estimator 13, and the balance controller 14 (the later-described shortest route controller 15, alternative route controller 16, and activity adjustment controller 17) process signals inputted to these components by the CPU in accordance with the computer programs stored in the ROM and operate as described later.

Based on a detection signal detected by the movement amount sensor 4, the somatic nervous system activity detector 11 detects the physical activity, i.e., the somatic nervous system activity t of the driver in association with steering of the vehicle V.

Specifically, when a wheel speed sensor (speed sensor) or a time measuring sensor is used as the movement amount sensor 4, the somatic nervous system activity detector 11 detects, as the somatic nervous system activity t, a ratio (lap time ratio) of a measured lap time, which is the comparison target, to a reference lap time previously measured in a predetermined driving course.

When a steering angle sensor is used as the movement amount sensor 4, the somatic nervous system activity detector 11 detects, as the somatic nervous system activity t, smoothness of steering operation calculated by using a differential value or the like of time-series data of the steering angle sensor.

Note that the somatic nervous system activity t may be detected based on a detection signal of the muscle activity strength detected by the perception amount controller 2, or based on a steering angle detection signal detected by the sound effect generator 3. In the case where the detection signal of the voluntary movement amount is inputted from the perception amount controller 2 or the sound effect generator 3, the movement amount sensor 4 can be omitted.

Based on a detection signal detected by the vital sensor 5, the autonomic nervous system activity detector 12 detects the mental activity, i.e., the autonomic nervous system activity g of the driver in association with the steering of the vehicle V.

Specifically, when a heart rate sensor is used as the vital sensor 5, a ratio (heart rate ratio) of a measured heart rate, which is the comparison target, to a previously measured heart rate in a rest state is detected as the autonomic nervous system activity g.

Note that as the vital sensor 5, an existing sensor such as a pupil diameter measurement device for measuring a pupil diameter of a driver from a captured image, a device for measuring a quantity of electricity of skin, a blood pressure measurement device, and a perspiration amount measurement device may be used. Alternatively, a sensor which is capable of directly conducting electrical measurement of an activity amount (degree of activation) of the sympathetic nerves or the parasympathetic nerves may be used as the vital sensor 5.

The driver's state estimator 13 receives input of information of the somatic nervous system activity t detected by the somatic nervous system activity detector 11 and information of the autonomic nervous system activity g detected by the autonomic nervous system activity detector 12, and based on the inputted somatic nervous system activity t and autonomic nervous system activity g, estimates the psychosomatic state of the driver.

Figure 3:
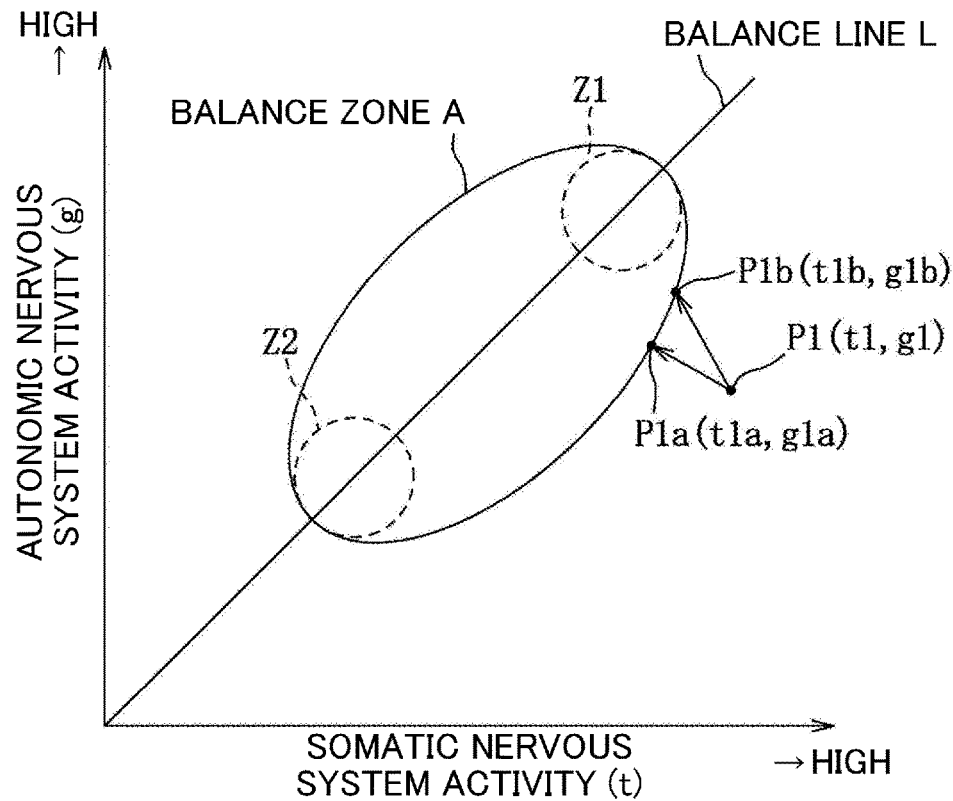
FIG. 3 is a diagram for explaining a control route from outside to inside of a balance zone in a coordinate system defined by a somatic nervous system activity and an autonomic nervous system activity.
Figure 4:
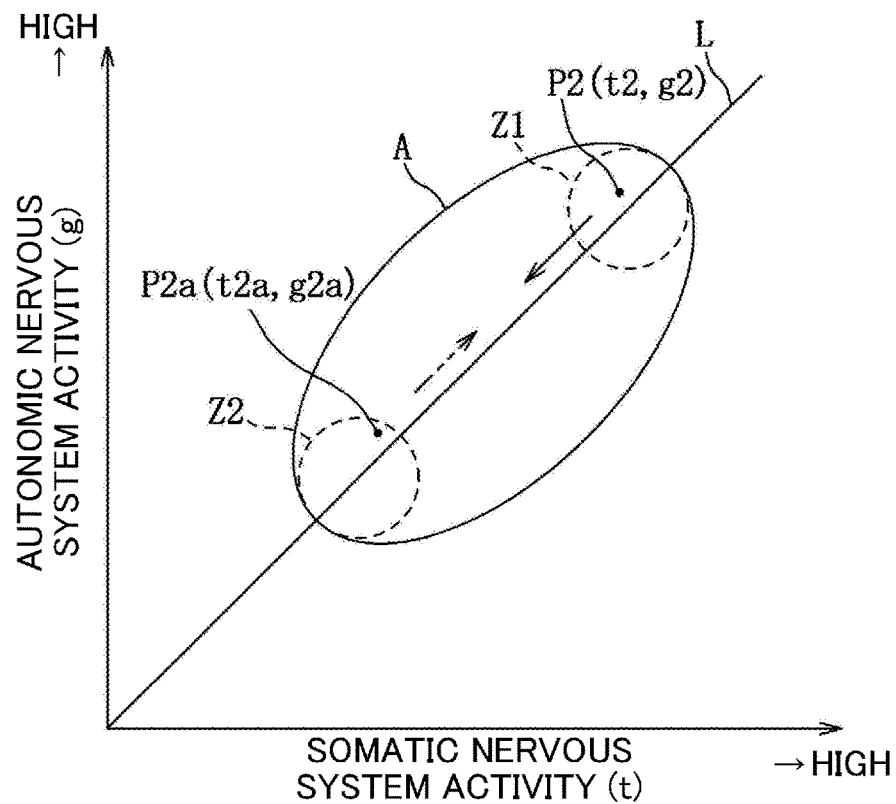
FIG. 4 is a diagram for explaining a control route inside the balance zone in the coordinate system.

As shown in FIGS. 3 and 4, the driver's state estimator 13 determines a psychosomatic state P of the driver by coordinates P (t, g) of the somatic nervous system activity t and autonomic nervous system activity g in a two-dimensional coordinate system defined by the somatic nervous system activity t and the autonomic nervous system activity g (orthogonal coordinate system in which a horizontal axis represents the somatic nervous system activity t and a vertical axis represents the autonomic nervous system activity g).

In the coordinate system, since the somatic nervous system activity t indicates an amount which is perceived by a sense through physical movement, a region in which the somatic nervous system activity t is high and the autonomic nervous system activity g is low corresponds to a region in which as compared with excitement of mind, reaction to operation is strong, for example, a region in which an operation burden is sensuously large for the driver or the driver feels bored.

On the other hand, a region in which the somatic nervous system activity t is low and the autonomic nervous system activity g is high corresponds to a region in which as compared with the excitement of mind, the reaction to operation is weak, for example, a region in which a sense of disappointment is sensuously large for the driver or the driver feels uneasy.

In the coordinate system, a balance line L on which a ratio of the autonomic nervous system activity g to the somatic nervous system activity t is constant and an elliptical balance zone A whose center is located on the balance line L are previously set.

The balance line L is set in the following manner. In a state in which both the mind and body of the driver are activated, that is, in which a sense of self-efficacy is high, a somatic nervous system activity t and an autonomic nervous system activity g are previously detected as reference samples by experiments, empirical values, or the like. A line connecting coordinates (t, g) corresponding to these somatic nervous system activity t and autonomic nervous system activity g and the origin is set as the balance line L.

The balance zone A is set such that its long axis is superposed on the balance line L and a short axis is orthogonal to the balance line L. The balance zone A is set in a middle region of the balance line, except the vicinity of the upper end and the vicinity of the lower end of the balance line L. Thus, when the coordinates P (t, g) are located inside the balance zone A (or on the elliptical outline thereof), the driver is in a state in which his/her mind and body are both activated and the sense of self-efficacy is high.

When a heart rate is detected as the autonomic nervous system activity g, the balance zone A is set in a region corresponding to a heart rate of, for example, 80 to 140 (beats/min.).

The driver's state estimator 13 defines coordinates (t, g) of the somatic nervous system activity t and the autonomic nervous system activity g in the coordinate system as coordinates P (t, g) which represent a psychosomatic state P of the driver and estimates the psychosomatic state P of the driver based on positional relationship between the coordinates P (t, g) and the balance zone A.

Figure 11:
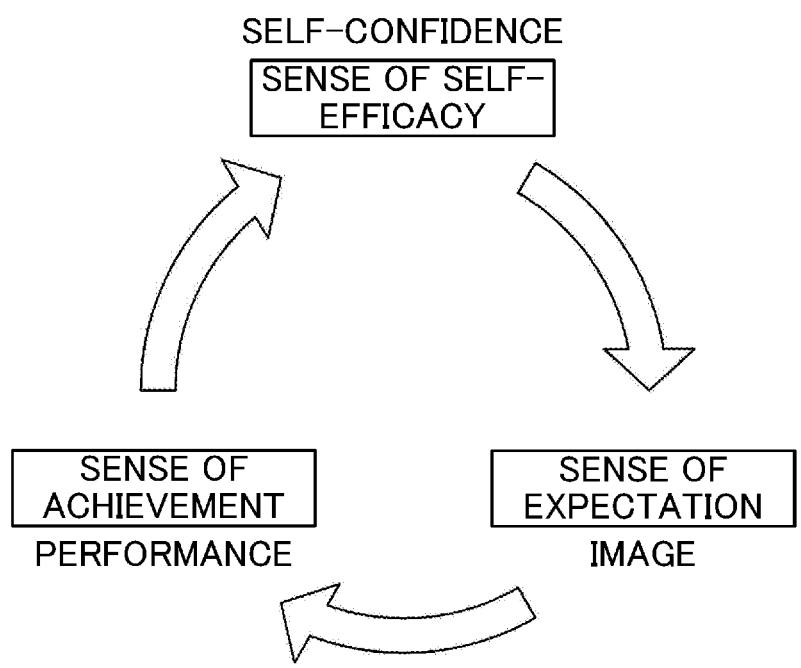
FIG. 11 is a conceptual diagram showing an idea of the present invention.

When the coordinates P (t, g) representing the psychosomatic state P of the driver are present inside the balance zone A, the driver's state estimator 13 determines that the driver is in a state where the somatic nervous system and the autonomic nervous system are activated in a balanced manner (i.e., in a state where the activation circle comprised of three factors shown in FIG. 11, namely, a sense of expectation, a sense of achievement, and a sense of self-efficacy, smoothly circulate, and intrinsic motivation is generated). When the coordinates P (t, g) are present inside the balance zone A and on the balance line L, the driver's state estimator 13 determines that the driver is in a state where the somatic nervous system and the autonomic nervous system are activated in a most favorable manner.

Conversely, when the coordinates P (t, g) representing the psychosomatic state P of the driver are present outside the balance zone A, the driver's state estimator 13 determines that the driver is in a state where the somatic nervous system and the autonomic nervous system have lost balance and that the larger a distance from the balance zone A is, the worse the psychosomatic state has become.

Hereinafter, unless otherwise described, the psychosomatic state P of the driver is referred to as the state P, and the state P is represented by the coordinates P (t, g) in the coordinate system.

Based on the state P estimated by the driver's state estimator 13 (that is, based on the somatic nervous system activity t detected by the somatic nervous system activity detector 11 and the autonomic nervous system activity g detected by the autonomic nervous system activity detector 12), the balance controller 14 controls the perception amount controller 2 as a somatic nervous system activity controller and the sound effect generator 3 as an autonomic nervous system activity controller. Specifically, based on information of the state P inputted from the driver's state estimator 13, the balance controller 14 causes at least one of the perception amount controller 2 or the sound effect generator 3 to operate, thereby transitioning a current state P to a state better than the current state P. As can be seen, the balance controller 14 is equivalent to a psychosomatic state controller which controls the state P by controlling the perception amount controller 2 and the sound effect generator 3.

As shown in FIG. 2, the balance controller 14 has the shortest route controller 15, the alternative route controller 16, and the activity adjustment controller 17.

In this embodiment, when the state P (coordinates P (t, g)) is present outside the balance zone A, the shortest route controller 15 operates or both the shortest route controller 15 and the alternative route controller 16 operate. When the coordinates P (t, g) are present inside the balance zone A, the activity adjustment controller 17 operates.

When current coordinates P (t, g) are present outside the balance zone A, the shortest route controller 15 sets target coordinates which are inside the balance zone A is and at the shortest distance from the current coordinates P (t, g). The shortest route controller 15 causes at least one of the perception amount controller 2 or the sound effect generator 3 to operate so that the coordinates P (t, g) shift toward the target coordinates based on the set shortest route. During execution of the shortest route controller 15, a flag F2 is set to 1, and upon finishing the execution, the flag F2 is set to 0 (see FIG. 7).

Based on the current coordinates P (t, g) and the target coordinates, the shortest route controller 15 calculates an amount of change (an amount of increase or decrease) in the somatic nervous system activity t and an amount of change (an amount of increase or decrease) in the autonomic nervous system activity g that are required to shift the current coordinates P to the target coordinates. The shortest route controller 15 then causes the perception amount controller 2 to operate in accordance with the amount of change in the somatic nervous system activity t and/or causes the sound effect generator 3 to operate in accordance with the amount of change in the autonomic nervous system activity g. Here, if the somatic nervous system activity t increases to shift the current coordinates P (t, g) to the target coordinates, the amount of change in the somatic nervous system activity t is represented as a positive value. If the somatic nervous system activity t decreases to shift the current coordinates P (t, g) to the target coordinates, the amount of change in the somatic nervous system activity t is represented as a negative value. The same applies for the amount of change in the autonomic nervous system activity g.

As shown in FIG. 3, for example, when current coordinates P1 (t1, g1) are present outside the balance zone A, the shortest route controller 15 calculates target coordinates P1$a$ (t1$a$, g1$a$) which are inside the balance zone A and at the shortest distance from the current coordinates P1 (t1, g1). From the current coordinates P1 (t1, g1) and the target coordinates P1$a$ (t1$a$, g1$a$), the shortest route controller 15 calculates a difference $\Delta t1$ (=t1$a$−t1) which corresponds to an amount of change in the somatic nervous system activity t and a difference $\Delta g1$ (=g1$a$−g1) which corresponds to an amount of change in the autonomic nervous system activity g, and causes the perception amount controller 2 to operate in accordance with the difference $\Delta t1$ and causes the sound effect generator 3 to operate in accordance with the difference $\Delta g1$. Note that when one of the difference $\Delta t1$ and the difference $\Delta g1$ is 0, one of the perception amount controller 2 and the sound effect generator 3, which is associated with the difference of 0, is not caused to operate.

Thus, the state P (coordinates (t, g)) is caused to shift toward the inside of the balance zone A within the shortest period of time.

Specifically, when the somatic nervous system activity t is to be increased, the shortest route controller 15 increases the voluntary movement amount (for example, by reducing a gear ratio of steering or increasing a reactive force perception amount of an accelerator pedal) via the perception amount controller 2, thereby improving an operation feeling. On the other hand, when the somatic nervous system activity t is to be reduced, the shortest route controller 15 reduces the voluntary movement amount (for example, by increasing the gear ratio of steering or reducing the reactive force perception amount of the accelerator pedal) via the perception amount controller 2, thereby reducing the perception amount of operation.

When the autonomic nervous system activity g is to be increased, the shortest route controller 15 causes uplift of driving consciousness of the driver (for example, by generating sound effects or increasing a gain of the sound effects) via the sound effect generator 3, thereby improving the following feeling. On the other hand, when the autonomic nervous system activity g is to be reduced, the shortest route controller 15 lowers the driving consciousness of the driver (for example, by stopping the sound effects or reducing the gain of the sound effects) via the sound effect generator 3, thereby reducing the following feeling.

When at least one of the amount of change in the somatic nervous system activity t or the amount of change in the autonomic nervous system activity g, calculated by the shortest route controller 15, is an amount of decrease (that is, a negative value) and the absolute value of the amount of decrease is equal to or greater than a predetermined value, the alternative route controller 16 sets an alternative route which makes the absolute value of the amount of change, which is equal to or greater than the predetermined value, become smaller than the predetermined value. The alternative route controller 16 then causes at least one of the perception amount controller 2 or the sound effect generator 3 to operate such that the coordinates P (t, g) shifts along the set alternative route. During execution of the alternative route controller 16, a flag F3 is set to 1, and upon finishing the execution, the flag F3 is set to 0 (see FIG. 7). Note that the predetermined value associated with the amount of change in the somatic nervous system activity t and the predetermined value associated with the amount of change in the autonomic nervous system activity g may be the same as each other or may be different from each other.

As shown in FIG. 3, for example, when the current coordinates P1 (t1, g1) are outside the balance zone A and the target coordinates for the shortest route are P1a (t1a g1a) as described above, since the amount of change in the autonomic nervous system activity g is an amount of increase, the change in the autonomic nervous system activity g increases the sense of expectation of the driver. However, since the amount of change in the somatic nervous system activity t is an amount of decrease, when the absolute value of the amount of change in the somatic nervous system activity t is equal to or greater than the predetermined value, the change in the somatic nervous system activity t significantly reduces the sense of achievement of the driver and it is likely that the driver feels a sense of discomfort.

In view of this, in order to inhibit the sense of achievement of the driver from being significantly reduced, the alternative route controller 16 changes the target coordinates inside the balance zone A to coordinates P1b (t1b, g1b) so as to make the amount of change in the somatic nervous system activity t have an absolute value which does not cause the driver to feel a sense of discomfort (that is, a value smaller than the predetermined value).

From the coordinates P1 (t1, g1) and the target coordinates P1b (t1b, g1b), the alternative route controller 16 calculates a difference Δt2 (=t1b−t1) whose absolute value is smaller than that of the difference Δt1 and a difference Δg2 (=g1b−g1), and causes the perception amount controller 2 to operate in accordance with the difference Δt2 and causes the sound effect generator 3 to operate in accordance with the difference Δg2.

As with the shortest route controller 15, when the somatic nervous system activity t is to be increased, the alternative route controller 16 also increases the voluntary movement amount via the perception amount controller 2 whereas when the somatic nervous system activity t is to be reduced, the alternative route controller 16 reduces the voluntary movement amount via the perception amount controller 2. In addition, when the autonomic nervous system activity g is to be increased, the alternative route controller 16 causes uplift of the driving consciousness of the driver via the sound effect generator 3 whereas when the autonomic nervous system activity g is to be reduced, the alternative route controller 16 lowers the driving consciousness of the driver via the sound effect generator 3. The same applies to the activity adjustment controller 17.

Thus, the state P (coordinates (t, g)) is shifted toward the inside of the balance zone A within a short period of time without allowing the driver to feel a sense of discomfort.

When the coordinates P (t, g) are present inside the balance zone A, the activity adjustment controller 17 causes the perception amount controller 2 and the sound effect generator 3 to operate such that the state P (coordinates P (t, g)) shifts parallel to the balance line L, that is, the somatic nervous system activity t and the autonomic nervous system activity g shift to the same side with respect to increase and decrease (i.e., both the somatic nervous system activity t and the autonomic nervous system activity g increase or decrease). Since the balance line L is a line on which the ratio of the autonomic nervous system activity g to the somatic nervous system activity t is constant, a ratio of the somatic nervous system activity t to the autonomic nervous system activity g is constant also on a shifting trajectory parallel to the balance line L. Note that in this embodiment, the activity adjustment controller 17 causes the perception amount controller 2 and the sound effect generator 3 to operate as described above when performing the later-described activity reducing control and activity increasing control.

As shown in FIGS. 3 and 4, an upper end zone Z1 is set in the vicinity of the upper end inside the balance zone A (a region in which both the somatic nervous system activity t and the autonomic nervous system activity g have maximum values or values approximate to the maximum values). A lower end zone Z2 is set in the vicinity of the lower end inside the balance zone A (a region in which both the somatic nervous system activity t and the autonomic nervous system activity g have minimum values or values approximate to the minimum values).

In the upper end zone Z1, although the somatic nervous system and the autonomic nervous system are activated in a balanced manner, a driving load is high and a degree of tension is high. Therefore, the upper end zone Z1 does not necessarily represent a state suitable for driving for a long time.

Therefore, when the state P (coordinates P (t, g)) is present inside the upper end zone Z1 for a period of time exceeding a fixed period of time (for example, when the state P is present on coordinates P2 (t2, g2) shown in FIG. 4 with no changes for a period of tome exceeding the fixed period), the activity adjustment controller 17 performs the activity reducing control for reducing both the somatic nervous system activity t and the autonomic nervous system activity g along a shifting trajectory parallel to the balance line L inside the balance zone A. In the activity reducing control of this embodiment, the somatic nervous system activity t and the autonomic nervous system activity g are not reduced at once to reach the lower end zone Z2, but are gradually reduced in a plurality of decrements to reach the lower end zone Z2 in order not to cause the driver to feel a sense of discomfort.

The activity reducing control serves to release the driver from a high load state of a long period of time and to ensure comfortability.

Once the state P (coordinates P (t, g)) has reached the lower end zone Z2 (in FIG. 4, coordinates P2a (t2a, g2a) during execution of the activity reducing control, the activity adjustment controller 17 then performs the activity increasing control for increasing both the somatic nervous system activity t and the autonomic nervous system activity g along the shifting trajectory parallel to the balance line L inside the balance zone A. In the activity increasing control, as with the activity reducing control, the somatic nervous system activity t and the autonomic nervous system activity g are gradually increased in a plurality of increments to reach the upper end zone Z1 in order not to cause the driver to feel a sense of discomfort.

The activity increasing control serves to increase the sense of self-efficacy.

Figure 7:
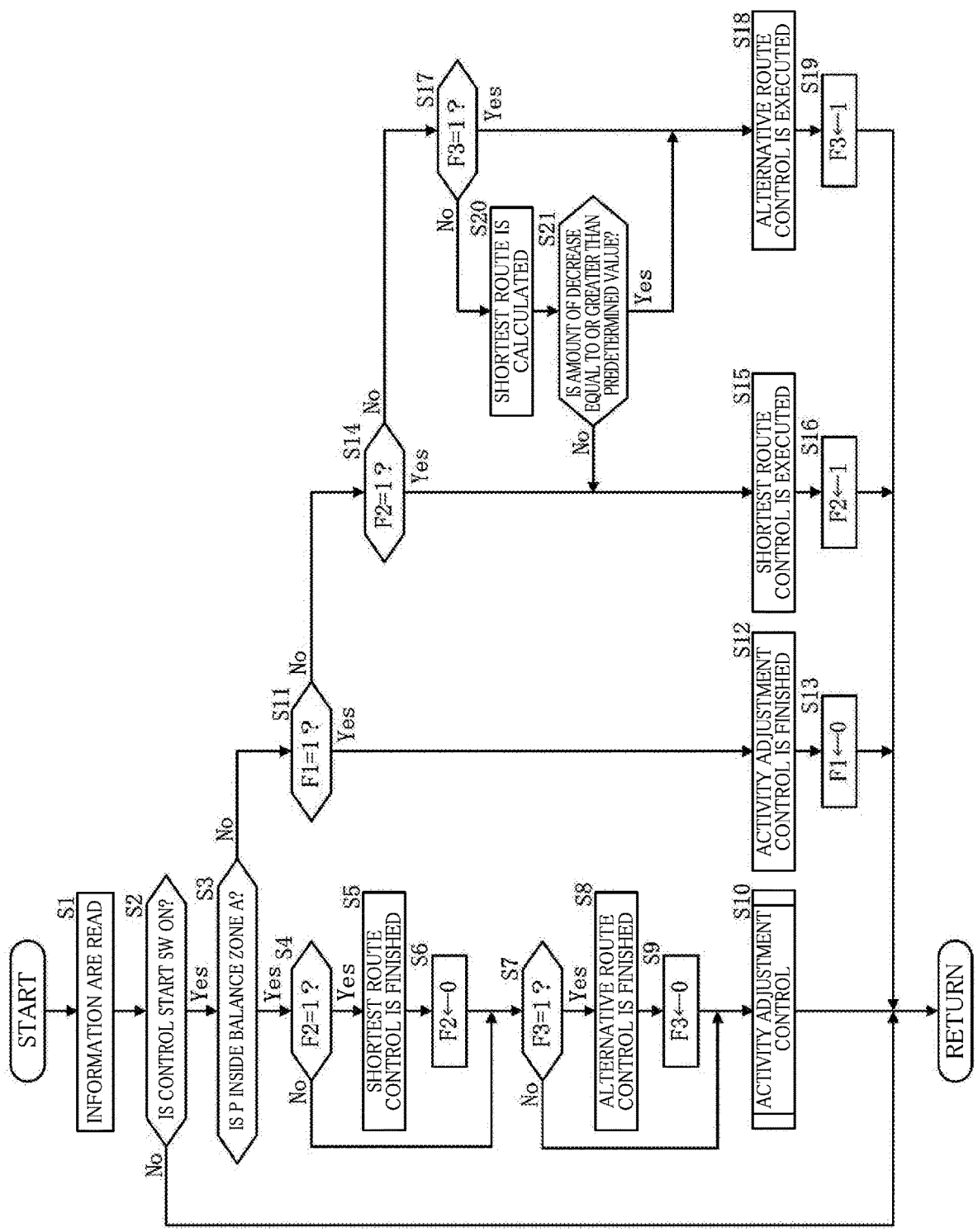
FIG. 7 is a flowchart showing a process of control performed by a driver's state estimator and a balance controller.
Figure 8:
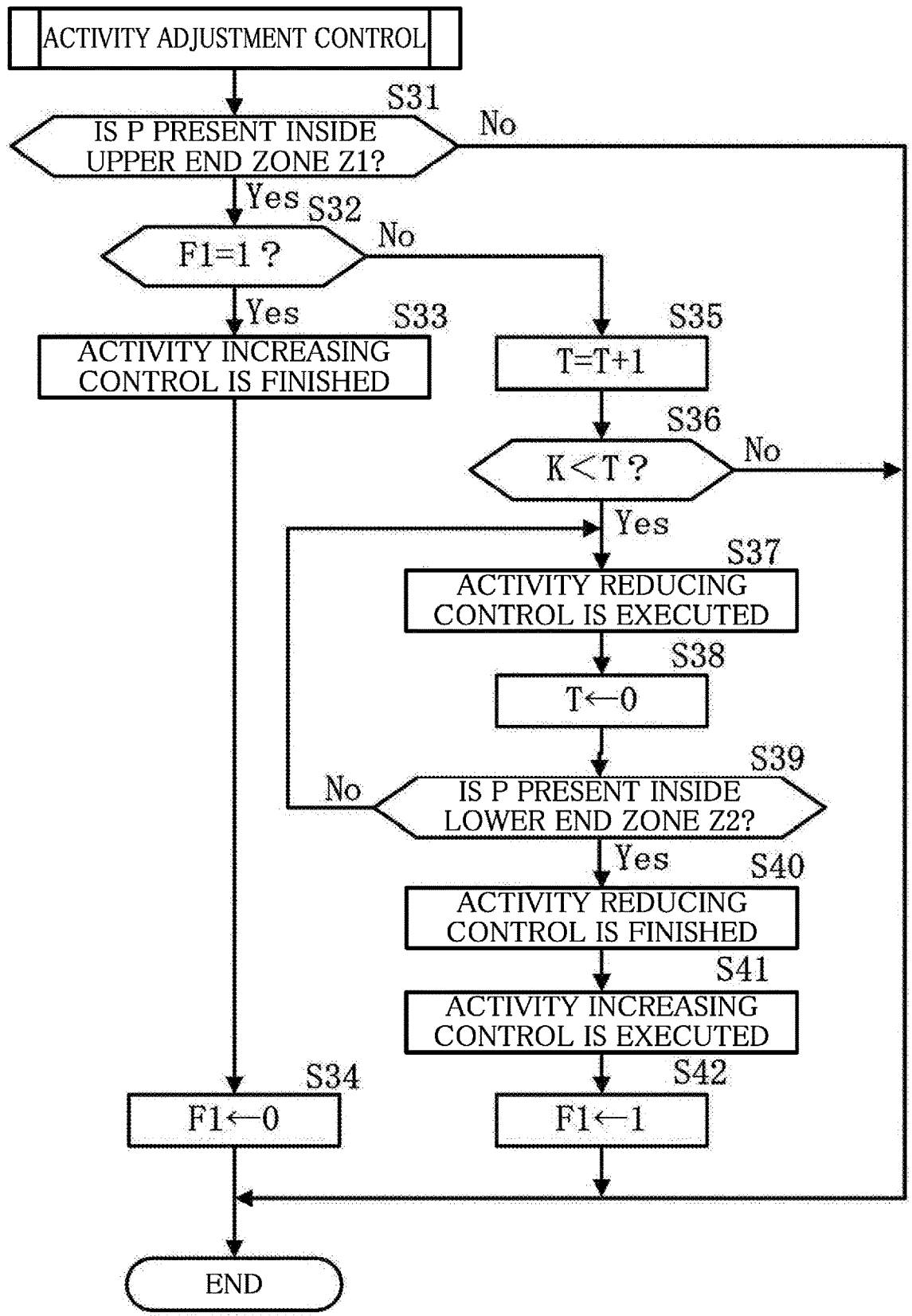
FIG. 8 is a flowchart showing details of a process of activity adjustment control carried out in Step S10 in the flowchart shown in FIG. 7.

During execution of the activity increasing control, a flag F1 is set to 1, and upon finishing the execution, the flag F1 is set to 0 (see FIGS. 7 and 8). During the execution of the activity increasing control, when the state P (coordinates P (t, g)) has reached the upper end zone Z1, the activity increasing control is finished.

The perception amount controller 2 controls a response perception amount which the driver perceives and which depends on behavior of the vehicle V, so that the response perception amount has linearity with respect to a reactive force perception amount of the operation apparatuses.

Figure 5:
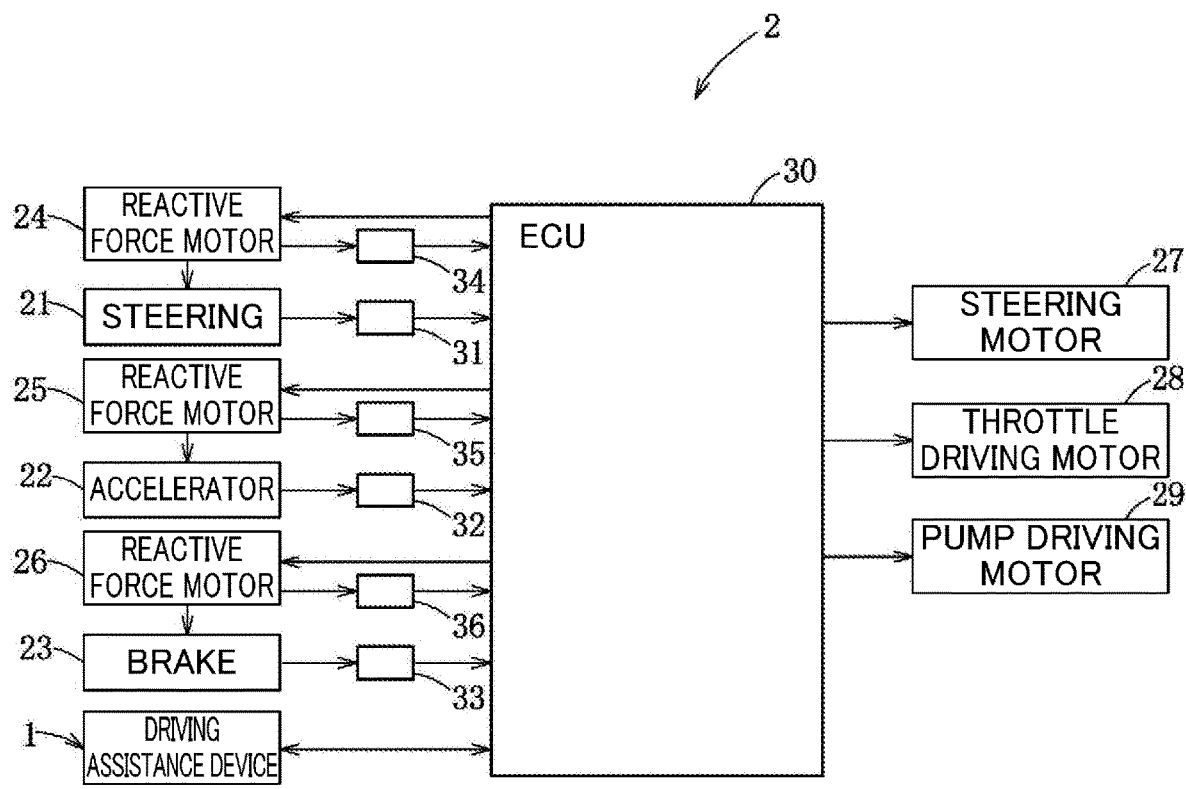
FIG. 5 is a block diagram illustrating a perception amount controller.

As shown in FIG. 5, the perception amount controller 2 includes: operation apparatuses operable by the driver, namely, a steering 21 (precisely speaking, a steering wheel), an accelerator 22 (precisely speaking, an accelerator pedal), and a brake 23 (precisely speaking, a brake pedal); reactive force motors 24 to 26, each of which provides a reactive force perception amount for the driver in accordance with an operation amount of an associated one of the operation apparatuses 21 to 23; a steering motor 27, a throttle driving motor 28, and a brake pump driving motor 29, each of which generates a response perception amount of the vehicle V in accordance with the operation amount of an associated one of the operation apparatuses 21 to 23; and an ECU 30 which controls the reactive force motors 24 to 26 and the motors 27 to 29. The operation amount of each of the operation apparatuses 21 to 23 is outputted as a detection signal of an associated one of operation amount sensors 31 to 33 to the ECU 30, and an operation force of each of the operation apparatuses 21 to 23 is outputted as a detection signal of an associated one of operation force sensors 34 to 36 to the ECU 30.

The ECU 30 is capable of optionally controlling a gear ratio of the steering 21 (a gear ratio between the steering 21 and front wheels) and the reactive force perception amount of the accelerator 22.

In this embodiment, when the somatic nervous system activity t is to be increased in a state in which the control start switch 6 is on, the ECU 30 switches the gear ratio of the steering 21 via a variable gear ratio (VGR) mechanism to a gear ratio (e.g., 11.0) smaller than a normal gear ratio (e.g., 14.5). When the somatic nervous system activity t is to be reduced in the state in which the control start switch 6 is on, the ECU 30 switches the gear ratio of the steering 21 to a gear ratio (e.g., 15.5) greater than the normal gear ratio.

Note that a detailed description of the specific configuration of the perception amount controller 2 is omitted herein since the present applicant has already filed a patent application directed to the perception amount controller (see Japanese Patent Application No. 2016-099456).

The sound effect generator 3 generates rumbling sound of the engine to state turning behavior of the vehicle V, thereby performing control to enhance a turning operation feeling.

Figure 6:
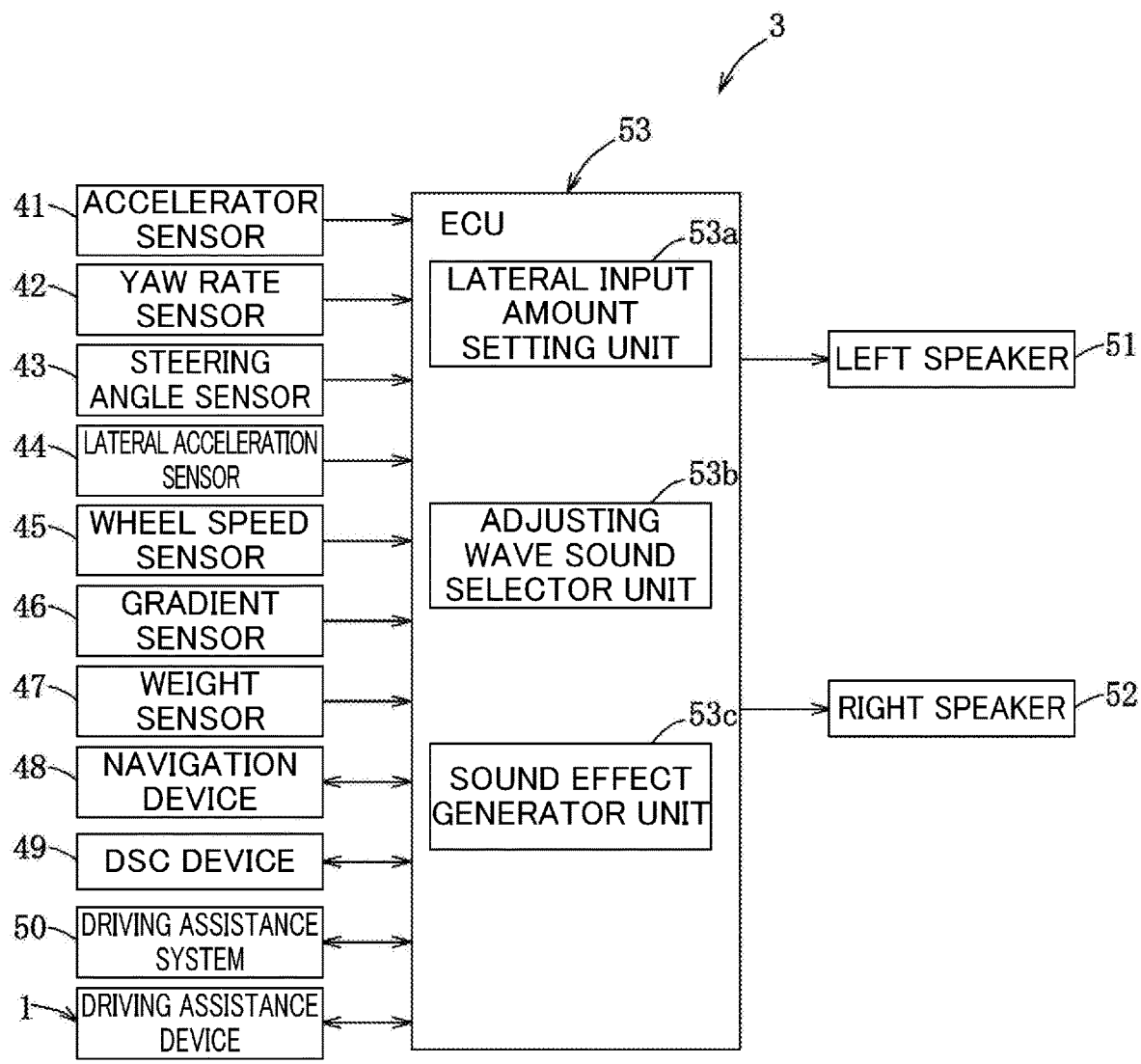
FIG. 6 is a block diagram illustrating a sound effect generator.

As shown in FIG. 6, the sound effect generator 3 includes a driving state detector which is comprised of an accelerator sensor 41, a yaw rate sensor 42, a steering angle sensor 43, a lateral acceleration sensor 44, a wheel speed sensor 45, a gradient sensor 46, a weight sensor 47, a navigation device 48, a differential scanning calorimetry device 49, and a driving assistance system 50; a left speaker 51 provided on a left side of the vehicle V and a right speaker 52 provided on a right side of the vehicle V (a pair of speakers); and an ECU 53. The ECU 53 has a lateral input amount setting unit 53a for setting, based on a traveling state detected by the yaw rate sensor 42 and the lateral acceleration sensor 44, a lateral input amount whose parameter is a physical quantity related to at least one of movement of the vehicle V in the vehicle width direction or movement thereof in a turning direction, an adjusting wave sound selector unit 53b for selecting, based on the lateral input amount, a plurality of half-order adjusting wave sounds comprised of half-order frequency components, and a sound effect generator unit 53c for synthesizing fundamental wave sounds and the selected plurality of half-order adjusting wave sounds.

The driving assistance system 50 has an inter-vehicular distance notification function and a driver emotion improvement function.

The adjusting wave sound selector unit 53b of the ECU 53 is capable of optionally controlling a gain of the plurality of half-order adjusting wave sounds.

In this embodiment, when the autonomic nervous system activity g is to be increased in the state in which the control start switch 6 is on, the adjusting wave sound selector unit 53b increases and compensates a compensation coefficient of a gain of the adjusting wave sounds in proportion to a degree of depression of the accelerator 22. When the autonomic nervous system activity g is to be reduced in the state in which the control start switch 6 is on, the adjusting wave sound selector unit 53b reduces and compensates the compensation coefficient of the gain of the adjusting wave sounds in proportion to the degree of depression of the accelerator 22.

Note that a detailed description of the specific configuration of the sound effect generator 3 is omitted herein since the present applicant has already filed a patent application directed to the sound effect generator (see Japanese Patent Application No. 2016-071382).

Next, with reference to flowcharts shown in FIGS. 7 and 8, processes of controlling carried out by the driver's state estimator 13 and the balance controller 14 will be described.

As shown in the flowchart in FIG. 7, first, in Step S1, various pieces of information are read. The various pieces of information to be read include pieces of information pertinent to a signal of the control start switch 6, the somatic nervous system activity t detected by the somatic nervous system activity detector 11, and the autonomic nervous system activity g detected by the autonomic nervous system activity detector 12.

In the subsequent Step S2, it is determined whether or not the control start switch 6 has been turned on.

If the result of the determination in Step S2 indicates that the control start switch 6 has been turned on, the process proceeds to Step S3.

If the result of the determination in Step S2 indicates that the control start switch 6 has not been turned on (i.e., is off), the process directly returns.

In Step S3, it is determined whether or not the state P is present inside the balance zone A.

If the result of the determination in Step S3 indicates that the state P is present inside the balance zone A, the process proceeds to Step S4.

In Step S4, it is determined whether or not the flag F2 has been set to 1.

If the result of the determination in Step S4 indicates that the flag F2 has been set to 1, it is meant that despite the presence of the state P inside the balance zone A, the shortest route control is under execution. The process then proceeds to Step S5 where the shortest route control is finished. In Step S6 subsequent to Step S5, the flag F2 is set to 0, and thereafter, the process proceeds to Step S7.

If the result of the determination in Step S4 indicates that the flag F2 has not been set to 1 (i.e., the flag F2 is 0), the process proceeds to Step S7.

In Step S7, it is determined whether or not the flag F3 has been set to 1.

If the result of the determination in Step S7 indicates that the flag F3 has been set to 1, it is meant that despite the presence of the state P inside the balance zone A, the alternative route control is under execution. The process then proceeds to Step S8 where the alternative route control is finished. In step S9 subsequent to Step S8, the flag F3 is set to 0, and thereafter, the process proceeds to Step S10.

If the result of the determination in Step S7 indicates that the flag F3 has not been set to 1 (i.e., the flag F3 is 0), the process proceeds to Step S10.

In Step S10, the activity adjustment control is executed, and thereafter, the process returns.

If the result of the determination in Step S3 indicates that the state P is not present inside the balance zone A (i.e., is present outside the balance zone A), the process proceeds to Step S11.

In Step S11, it is determined whether or not the flag F1 has been set to 1.

If the result of the determination in Step S11 indicates that the flag F1 has been set to 1, it is meant that despite the presence of the state P inside the balance zone A, the activity increasing control is under execution. The process then proceeds to Step S12 where the activity increasing control is finished. The flag F1 is set to 0 in the subsequent Step S13, and thereafter, the process returns.

If the result of the determination in Step S11 indicates that the flag F1 has not been set to 1 (i.e., the flag F1 is 0), the process proceeds to Step S14 where it is determined whether or not the flag F2 has been set to 1.

If the result of the determination in Step S14 indicates that the flag F2 has been set to 1, it is meant that the shortest route control is already under execution. Therefore, the execution of the shortest route control is continued in Step S15. The flag F2 is allowed to remain 1 in the subsequent Step S16, and thereafter, the process returns.

If the result of the determination in Step S14 indicates that the flag F2 has not been set to 1 (i.e., the flag F2 is 0), the process proceeds to Step S17 where it is determined whether or not the flag F3 has been set to 1.

If the result of the determination in Step S17 indicates that the flag F3 has been set to 1, it is meant that the alternative route control is already under execution. Therefore, the execution of the alternative route control is continued in Step S18. The flag F3 is allowed to remain 1 in the subsequent Step S19, and thereafter, the process returns.

If the result of the determination in Step S17 indicates that the flag F3 has not been set to 1 (i.e., the flag F3 is 0), it is meant that despite the presence of the state P outside the balance zone A, neither of the shortest route control and the alternative route control has been executed yet. The process then proceeds to Step S20.

In Step S20, the shortest route (target coordinates) from the state P (coordinates P (t, g)) to the balance zone A is calculated, and the process proceeds to the subsequent Step S21.

In Step S21, from the state P (coordinates P (t, g)) and the target coordinates of the shortest route, an amount of change in the somatic nervous system activity t and an amount of change in the autonomic nervous system activity g that are required for shifting to the target coordinates are calculated, and it is determined whether or not at least one of the amount of change in the somatic nervous system activity t or the amount of change in the autonomic nervous system activity g is an amount of decrease and whether the amount of decrease (here, the absolute value) is equal to or greater than the predetermined value.

If the result of the determination in Step S21 indicates that the amount of decrease (the absolute values) is equal to or greater than the predetermined value, the process shifts to Step S18 where the alternative route control is executed. The flag F3 is set to 1 in the subsequent Step S19, and thereafter, the process returns.

If the result of the determination in Step S21 indicates that the amount of change in the somatic nervous system activity t and the amount of change in the autonomic nervous system activity g are not amounts of decrease or that at least one of these amounts of change is an amount of decrease but the amount of decrease (the absolute value thereof) is less than the predetermined value, the process proceeds to Step S15 where the shortest route control is executed. The flag F2 is set to 1 in the subsequent Step S16, and thereafter, the process returns.

Next, with reference to the flowchart in FIG. 8, the activity adjustment control executed in Step S10 will be described in detail.

In the activity adjustment control, first, in Step S31, it is determined whether or not the state P is present inside the upper end zone Z1.

If the result of the determination in Step S31 indicates that the state P is present inside the upper end zone Z1, the process proceeds to Step S32 where it is determined whether or not the flag F1 has been set to 1.

If the result of the determination in Step S31 indicates that the state P is not present inside the upper end zone Z1, it is meant that the state P represents a state in which the sense of self-efficacy is high and which is suited for driving. Thus, the activity adjustment control is finished.

If the result of the determination in Step S32 indicates that the flag F1 has been set to 1, it is meant that the activity increasing control is under execution after the completion of the activity reducing control. The process then proceeds to Step S33 where the activity increasing control is finished. The flag F1 is set to 0 in the subsequent Step S34, and thereafter, the activity adjustment control is finished.

If the result of the determination in Step S32 indicates that the flag F1 has not been set to 1 (i.e., the flag F1 is 0), it is meant that the state P has first entered the upper end zone Z1. Therefore, the process proceeds to Step S35 where 1 is added to a timer T.

In the subsequent Step S36, it is determined whether or not the timer T has exceeded a determination value K.

If the result of the determination in Step S36 indicates that the timer T has exceeded the determination value K, it is meant that the state P has been present inside the upper end zone Z1 for a period of time exceeding a fixed period of time. Then, the activity reducing control is executed in Step S37. In the subsequent Step S38, the timer T is reset.

In the subsequent Step S39, it is determined whether or not the state P is present inside the lower end zone Z2.

If the result of the determination in Step S39 indicates that the state P is present inside the lower end zone Z2, it is meant that a load on the driver has been eliminated. The activity reducing control is then finished in Step S40.

If the result of the determination in Step S39 indicates that the state P is not present inside the lower end zone Z2, the process returns to Step S37.

In Step S41 subsequent to Step S40, in order to transition the state P to a state in which the sense of self-efficacy is high, the activity increasing control is executed. The flag F1 is set to 1 in the subsequent Step S42, and thereafter, the activity adjustment control is finished.

Next, operation and effects of the driving assistance device 1 according to this embodiment will be described.

For the description of the operation and effects, two kinds of verification experiments were conducted to two standard test subjects X and Y (drivers).

In a first verification experiment, each of the test subjects X and Y drove on a test course (circuit), so that a lap time was measured, and a ratio of this lap time to a reference lap time (lap time ratio) and a heart rate ratio were measured.

In a second verification experiment, each of the test subjects X and Y drove on the test course (circuit), so that smoothness of steering operation and a heart rate ratio were measured.

The first and second verification experiments were conducted to each of the test subjects X and Y, using vehicles (X1, Y1) each having a gear ratio of steering set to a normal ratio (e.g., 14.5), vehicles (X2, Y2) each including the perception amount controller 2 and having a gear ratio of steering set to a quick ratio (e.g., 11.0), and vehicles (X3, Y3) each including the sound effect generator 3 and having a gear ratio of steering set to the quick ratio, respectively.

Figure 9:
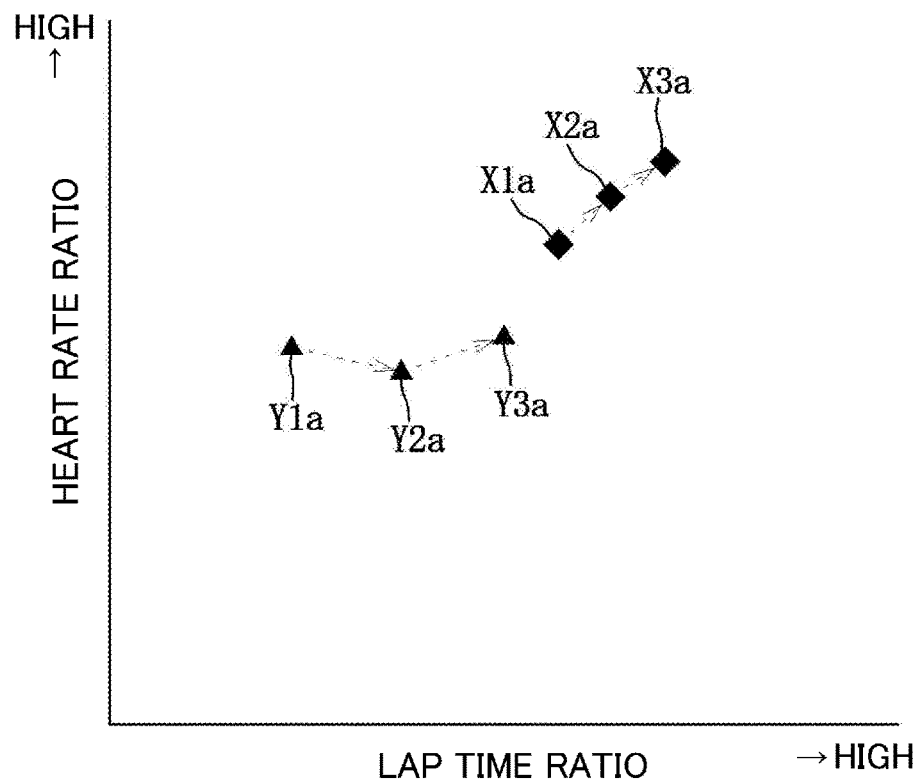
FIG. 9 is a graph showing relationship between a lap time ratio and a heart rate ratio, the relationship obtained through a first verification experiment.
Figure 10:
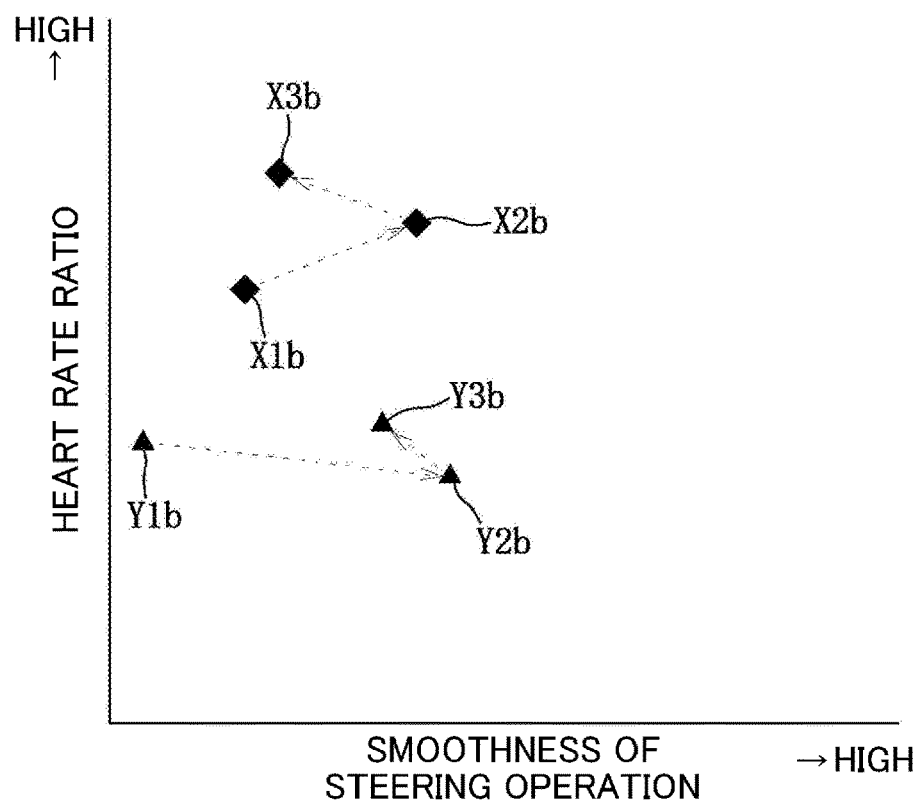
FIG. 10 is a graph showing relationship between smoothness of steering operation and a heart rate ratio, the relationship obtained through a second verification experiment.

With reference to FIGS. 9 and 10, the results of the first and second verification experiments will be described.

As shown in FIG. 9, the test subject X exhibited a higher lap time ratio in each of states X2$a$ and X3$a$ in which the gear ratio was set to the quick ratio than in a state X1$a$ in which the gear ratio was set to the normal ratio. In addition, the test subject X exhibited a higher heart rate ratio in the state X3$a$ in which sound effects were operative than the state Xa2 in which the sound effects were not operative.

Similarly, the test subject Y exhibited a higher lap time ratio in each of states Y2$a$ and Y3$a$ in which the gear ratio was set to the quick ratio than in a state Y1$a$ in which the gear ratio was set to the normal ratio. In addition, the test subject Y exhibited a higher heart rate ratio in the state Y3$a$ in which the sound effects were operative than the state Y2$a$ in which the sound effects were not operative.

Thus, it has been found that a decrease in the gear ratio of steering, that is, an increase in the perception amount of operation leads to an increase in the somatic nervous system activity t. In addition, it has been found that making the sound effects operative, that is, generating the rumbling sound of the engine allows the behavior of the vehicle in conjunction with operation of the driver to be clearly perceived, the following feeling of the behavior of the vehicle in response to the operation of the driver is enhanced, and that consequently, the autonomic nervous system activity g increases.

As shown in FIG. 10, the test subject X exhibited greater smoothness of steering operation in each of states X2$b$ and X3$b$ in which the gear ratio was set to the quick ratio than in a state X1$b$ in which the gear ratio was set to the normal ratio. In addition, the test subject X exhibited a higher heart rate ratio in the state X3$b$ in which the sound effects were operative than in the state X2$b$ in which the sound effects were not operative.

Similarly, the test subject Y exhibited higher smoothness of steering operation in each of states Y2$b$ and Y3$b$ in which the gear ratio was set to the quick ratio than in a state Y1$b$ in which the gear ratio was set to the normal ratio. In addition, the test subject Y exhibited a higher heart rate ratio in the state Y3$b$ in which the sound effects were operative than in the state of Y2$b$ in which the sound effects were not operative.

As with the results of the first verification experiment, it has been found that an increase in the perception amount of operation leads to an increase in the somatic nervous system activity t, and that and increase in the following feeling leads to an increase in the autonomic nervous system activity g.

Further, it has turned out that an increase in the following feeling due to making the sound effects operative may exert action to reduce the perception amount of operation depending on a driving situation.

In this embodiment, the driving assistance device 1 includes: the somatic nervous system activity detector 11 detecting the somatic nervous system activity t that is a physical activity of the driver in association with the steering of the vehicle V via the movement amount sensor 4; the autonomic nervous system activity detector 12 detecting the autonomic nervous system activity g that is a mental activity of the driver in association with the steering of the vehicle V via the vital sensor 5; the perception amount controller 2 as the somatic nervous system activity controller which is operable to control the somatic nervous system activity t; the sound effect generator 3 as the autonomic nervous system activity controller which is operable to control the autonomic nervous system activity g; and the balance controller 14 of the ECU 7 as the psychosomatic state controller which controls the somatic nervous system activity controller and the autonomic nervous system activity controller. Therefore, the driving assistance device 1 is operable to perform the control by visualizing the somatic nervous system activity t as numerical values via perception, movement, and action indices and is operable to perform the control by visualizing the autonomic nervous system activity g as numerical values via the physical internal indices.

Since the activity adjustment controller 17 of the balance controller 14 causes the perception amount controller 2 and the sound effect generator 3 to operate such that the somatic nervous system activity t and the autonomic nervous system activity g shift to the same side with respect to the increase and decrease, the somatic nervous system activity t and the autonomic nervous system activity g can be made to have the same tendency of increase or decrease. As a result, the state P of the driver can be transitioned to a state in which both his/her mind and body are activated without causing the driver to feel a sense of discomfort.

In addition, in this embodiment, since the activity adjustment controller 17 of the balance controller 14 causes the perception amount controller 2 and the sound effect generator 3 to operate such that the ratio between the somatic nervous system activity t and the autonomic nervous system activity g is constant, the state P of the driver can be easily brought into a state in which the somatic nervous system and the autonomic nervous system are activated in a balanced manner.

Further, in this embodiment, the coordinate system is defined by the somatic nervous system activity t and the autonomic nervous system activity g, and the balance zone A previously set so as to include part of the balance line L is provided in the coordinate system. When the somatic nervous system activity t and the autonomic nervous system activity g are present outside the balance zone A, the shortest route controller 15 and the alternative route controller 16 of the balance controller 14 cause the perception amount controller 2 and/or the sound effect generator 3 to operate such that the somatic nervous system activity t and the autonomic nervous system activity g shift to enter the balance zone A.

Thus, the state P of the driver can be observed in the coordinate system that is provided with the balance zone A including part of the balance line L representing a state in which the somatic nervous system and the autonomic nervous system are balanced. In addition, the state P of the driver can be easily brought into the state in which the somatic nervous system and the autonomic nervous system are activated in a balanced manner.

Furthermore, in this embodiment, when the somatic nervous system activity t and the autonomic nervous system activity g are present in the vicinity of the upper end (upper end zone Z1) inside the balance zone A in the coordinate system for a period of time exceeding the fixed period of time, the activity adjustment controller 17 reduces the somatic nervous system activity t and the autonomic nervous system activity g inside the balance zone A, and thereafter, increases the somatic nervous system activity t and the autonomic nervous system activity g. Therefore, a state in which the load on the driver is high can be avoided, and both the psychosomatically activated state of the driver and comfortability for the driver can be attained.

Further, in this embodiment, the perception amount controller 2 controls the gear ratio of steering that is the reactive force perception amount with respect to the operation amount of the driver, and the sound effect generator 3 controls the audiovisual perception amount with respect to the operation amount of the driver. Consequently, the state P of the driver can be quickly transitioned to the state in which both the mind and body of the driver are activated.

Furthermore, in this embodiment, since the somatic nervous system activity detector 11 detects the voluntary movement amount of the driver and the autonomic nervous system activity detector 12 detects the vital information of the autonomic nervous system of the driver, the somatic nervous system activity t and the autonomic nervous system activity g can be accurately detected in the form of numerical values.

The present invention is not limited to the embodiment described above. Any substitution can be made within the scope of the claims.

For example, in the embodiment described above, the lap time ratio and the smoothness of the steering have been described as examples of the voluntary movement amounts corresponding to the parameters of the somatic nervous system activity t. However, the present invention is not limited thereto. The voluntary movement amount may be, for example, a movement time other than the lap time ratio, a muscle activity strength related to an operation apparatus such as the steering wheel, the accelerator pedal, the brake pedal, the clutch pedal, and the shift lever, or the sight line movement speed. Alternatively, the voluntary movement amount may be a composite value of the foregoing.

In addition, the somatic nervous system activity t may be measured as brain activity related to a degree of concentration on a movement task. For example, somatosensory evoked magnetic fields (SEF) generated by somatic nervous system activity current can be measured by using magnetoencephalography (MEG). In addition, an electric phenomenon of several hundred μV as sinusoidal wave components of 1 Hz to 100 Hz generated in cortical cells can be measured by using dense array electroencephalogram (EEG). Further, a myoelectric potential (with EMG) of legs and arms or a motor evoked potential (MEP) may be directly measured.

In the embodiment described above, the heart rate ratio has been described as an example of the vital information of the autonomic nervous system. However, the present invention is not limited thereto. The vital information of the autonomic nervous system may be detection values of a heart rate, a blood pressure, perspiration, a pupil diameter, and the like.

Further, in the embodiment described above, the example has been described in which the perception amount controller 2 is used as the somatic nervous system activity controller and the sound effect generator 3 is used as the autonomic nervous system activity controller. However, it is only required for the somatic nervous system activity controller to be operable to control at least the operation feeling of the driver, and it is only required for the autonomic nervous system activity controller to be operable to control at least the following feeling of the behavior of the vehicle V in response to the operation of the driver.

In other words, as the somatic nervous system activity controller, a VGR steering system, an accelerator depression amount controller (or an accelerator depression force controller), a brake depression amount controller (or a brake depression force controller), or the like can be optionally selected. In addition, as the autonomic nervous system activity controller, a head-up display which controls a speed feeling of the driver by displaying an optical flow, a meter panel which controls the speed feeling of the driver by changing speed display, or the like can be optionally selected.

In addition, in the embodiment described above, the example has been described in which the activity adjustment controller 17 causes the perception amount controller 2 and the sound effect generator 3 to operate such that inside the balance zone A in the coordinate system, the somatic nervous system activity t and the autonomic nervous system activity g shift to the same side with respect to increase and decrease. However, the activity adjustment controller 17 may cause the perception amount controller 2 and the sound effect generator 3 to operate such that also outside the balance zone A, the somatic nervous system activity t and the autonomic nervous system activity g shift to the same side with respect to increase and decrease.

In this case, on the condition that the somatic nervous system activity t and the autonomic nervous system activity g shift to the same side with respect to increase and decrease, as with the shortest route control and the alternative route control, the activity adjustment controller 17 shifts the somatic nervous system activity t and the autonomic nervous system activity g from outside to inside of the balance zone A. When the condition cannot be satisfied for shifting to the inside of the balance zone A, the shifting is forbidden.

Further, in the embodiment described above, the example has been described in which the shape of the balance zone A in the coordinate system is elliptical. However, the shape and the region of the balance zone A in the coordinate system can be optionally set in accordance with specifications. The balance zone A may be, for example, in a rectangle shape whose center (center of gravity) is located on the balance line L and whose two sides facing each other are parallel to the balance line L, or may be in a cocoon shape which is symmetric with respect to the balance line L.

The foregoing embodiment is merely an example in nature, and the scope of the present invention should not be interpreted in a limited manner. The scope of the present invention is defined by the appended claims, and all variations and modifications belonging to a range equivalent to the range of the claims are within the scope of the present invention.

INDUSTRIAL APPLICABILITY

The present invention is useful as a driving assistance device that assists driving of a driver of a vehicle and, in particular, to a driving assistance device that determines a psychosomatic state of a driver of a vehicle based on a somatic nervous system activity and an autonomic nervous system activity of the driver and activates the psychosomatic state.

DESCRIPTION OF REFERENCE CHARACTERS

V Vehicle
A Balance Zone
L Balance Line
t Somatic Nervous System Activity
g Autonomic Nervous System Activity
1 Driving Assistance Device
2 Perception Amount Controller (Somatic Nervous System Activity Controller)
3 Sound Effect Generator (Autonomic Nervous System Activity Controller)
7 ECU
11 Somatic Nervous System Activity Detector
12 Autonomic Nervous System Activity Detector
13 Driver's Sate Estimator
14 Balance Controller (Psychosomatic State Controller)

The invention claimed is:

1. A driving assistance device for assisting driving of a driver of a vehicle, the driving assistance device comprising:
   a somatic nervous system activity detector detecting a somatic nervous system activity, which is a physical activity, of the driver in association with steering of the vehicle;
   an autonomic nervous system activity detector detecting an autonomic nervous system activity, which is a mental activity, of the driver in association with the steering of the vehicle;
   a somatic nervous system activity controller being operable to control the somatic nervous system activity;
   an autonomic nervous system activity controller being operable to control the autonomic nervous system activity; and
   a psychosomatic state controller controlling the somatic nervous system activity controller and the autonomic nervous system activity controller based on the somatic nervous system activity detected by the somatic nervous system activity detector and the autonomic nervous system activity detected by the autonomic nervous system activity detector, wherein
   the psychosomatic state controller is configured to cause the somatic nervous system activity controller and the autonomic nervous system activity controller to operate such that the somatic nervous system activity and the autonomic nervous system activity shift to a same side with respect to increase and decrease,
   a coordinate system is defined by the somatic nervous system activity and the autonomic nervous system activity,
   a balance zone previously set so as to include part of a balance line on which a ratio between the somatic nervous system activity and the autonomic nervous system activity is constant is provided in the coordinate system, and
   the psychosomatic state controller is configured such that when the somatic nervous system activity and the autonomic nervous system activity are present inside the balance zone, the psychosomatic state controller causes the somatic nervous system activity controller and the autonomic nervous system activity controller to operate such that the somatic nervous system activity and the autonomic nervous system activity shift to the same side with respect to increase and decrease, and
   when the somatic nervous system activity and the autonomic nervous system activity are present outside the balance zone, the psychosomatic state controller causes the somatic nervous system activity controller and/or the autonomic nervous system activity controller to operate such that the somatic nervous system activity and the autonomic nervous system activity shift to enter the balance zone.

2. The driving assistance device of claim 1, wherein the psychosomatic state controller is configured to cause the somatic nervous system activity controller and the autonomic nervous system activity controller to operate such that a ratio between the somatic nervous system activity and the autonomic nervous system activity is made constant.

3. The driving assistance device of claim 1 wherein the psychosomatic state controller is configured such that when the somatic nervous system activity and the autonomic nervous system activity are present in a vicinity of an upper end inside the balance zone in the coordinate system for a period of time exceeding a fixed period of time, the psychosomatic state controller causes the somatic nervous system activity controller and the autonomic nervous system activity controller to operate such the somatic nervous system activity and the autonomic nervous system activity increase after having decreased.

4. The driving assistance device of claim 1, wherein the somatic nervous system activity controller is configured to control a reactive force perception amount with respect to an operation amount of the driver, and
the autonomic nervous system activity controller is configured to control at least one of an audiovisual perception amount or a response speed with respect to the operation amount of the driver.

5. The driving assistance device of claim 1, wherein the somatic nervous system activity detector is configured to detect a voluntary movement amount of the driver, and
the autonomic nervous system activity detector is configured to detect vital information of the autonomic nervous system of the driver.

* * * * *